(12) United States Patent
Leibowitz et al.

(10) Patent No.: US 8,969,649 B2
(45) Date of Patent: Mar. 3, 2015

(54) INTEGRATED DRESSING DEVICE

(75) Inventors: Rebecca Leibowitz, Scotch Plains, NJ (US); Sandra Gensini, Flemington, NJ (US); Joseph Zavatsky, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 321 days.

(21) Appl. No.: 13/571,770

(22) Filed: Aug. 10, 2012

(65) Prior Publication Data
US 2014/0046238 A1    Feb. 13, 2014

(51) Int. Cl.
*A61F 13/00* (2006.01)
*A61F 13/02* (2006.01)
*A61M 25/02* (2006.01)

(52) U.S. Cl.
CPC ..... *A61F 13/00063* (2013.01); *A61F 13/00068* (2013.01); *A61F 13/023* (2013.01); *A61F 2013/00412* (2013.01); *A61M 2025/0266* (2013.01)
USPC ............. 602/58; 602/41; 602/42; 602/43; 602/48; 602/54; 602/57; 604/304

(58) Field of Classification Search
USPC ............ 604/174, 179, 180, 304–308; 602/41–59; 128/888, 889
See application file for complete search history.

(56) References Cited

U.S. PATENT DOCUMENTS

| | | | | |
|---|---|---|---|---|
| 2,955,331 A * | 10/1960 | Nelson | ........... | 118/268 |
| 2,969,144 A * | 1/1961 | Zackheim | ........... | 206/441 |
| 2,969,145 A * | 1/1961 | Hannauer, Jr. | ........... | 206/441 |
| 3,856,020 A | 12/1974 | Kovac | | |
| 3,918,446 A * | 11/1975 | Buttaravoli | ........... | 604/180 |
| 4,210,245 A * | 7/1980 | Dodge | ........... | 206/440 |
| 4,275,721 A * | 6/1981 | Olson | ........... | 604/180 |
| 4,324,237 A | 4/1982 | Buttaravoli | | |
| 4,915,694 A * | 4/1990 | Yamamoto et al. | ........... | 604/180 |
| 5,372,589 A | 12/1994 | Davis | | |
| 5,380,294 A | 1/1995 | Persson | | |
| 5,554,106 A * | 9/1996 | Layman-Spillar et al. | ..... | 602/42 |
| 5,833,665 A | 11/1998 | Bootman | | |
| 5,968,000 A | 10/1999 | Harrison | | |
| 6,765,122 B1 * | 7/2004 | Stout | ........... | 602/41 |
| 7,137,968 B1 * | 11/2006 | Burrell et al. | ........... | 604/180 |
| 7,723,561 B2 * | 5/2010 | Propp | ........... | 602/58 |
| 7,780,634 B2 * | 8/2010 | Propp | ........... | 604/180 |
| 8,569,567 B2 * | 10/2013 | Ovington | ........... | 602/42 |
| 2007/0123828 A1 * | 5/2007 | Propp | ........... | 604/180 |

FOREIGN PATENT DOCUMENTS

EP      2316395 A2    5/2011
WO    WO 98/10823 A1    3/1998

* cited by examiner

*Primary Examiner* — Kim M Lewis

(57) ABSTRACT

A device for the dressing of wounds and insertion sites of percutaneous and drug delivery devices provides 360 degree or complete circumferential protection of a wound or insertion site of a percutaneous or drug delivery device. In particular, the device is an integrated dressing for catheters comprising a pad and an adhesive dressing.

22 Claims, 7 Drawing Sheets

INTEGRATED DRESSING DEVICE

FIELD OF THE INVENTION

The invention relates to a device for the dressing of skin wounds and insertion sites of percutaneous as well as drug delivery devices. In particular, the device is an integrated dressing for percutaneous devices such as catheters comprising a pad and an adhesive dressing.

BACKGROUND OF THE INVENTION

Healthcare facilities employ multiple strategies to prevent and/or reduce infections associated with the use of percutaneous and drug delivery medical devices, which are devices that are temporarily left inside the body and that protrude out of the skin and exposed to the environment, in potential contact with microbial infection. Such strategies include topical cleansing at the site of insertion, use of antimicrobial dressings to protect the insertion site, prophylactic prescription of antibiotics, and use of catheters coated with antimicrobial agents, among others. There is evidence that protecting catheter insertion sites with antimicrobial dressings impregnated with antimicrobial agents, such as chlorhexidine gluconate, reduce skin colonization, which may be correlated to a lower incidence of catheter blood stream infections.

Many types of dressings are known for the treatment of wounds and insertion sites of percutaneous and drug delivery devices. Johnson & Johnson Corporation markets a commercially available product sold under the trademark BIO-PATCH® that is applied around percutaneous devices to prevent localized infection at the insertion site. This product is a foam material that contains the antimicrobial agent chlorhexidine gluconate (CHG). Efforts to coat the percutaneous and drug delivery medical devices with antimicrobial agents are also known.

Foam dressings (or pads) that protect insertion sites generally have an opening to conform around the percutaneous device. Depending on the size of the dressing and the percutaneous device, a transparent film is used to secure the dressing pad to the skin. The foam dressing and the transparent film come separately packaged, and the health care practitioner undertakes a two step process to dress the wound. First, the practitioner must open the package with the foam pad and apply it to the insertion site, and then the practitioner must open the package of the transparent dressing, remove the backing paper, and apply the transparent dressing over the foam dressing, all while keeping the insertion site clean and the patient potentially moving.

Transparent film dressings that allow a visual check on a catheter insertion site have recently been used as described in U.S. Pat. No. 5,372,589, issued Dec. 13, 1994 to Davis. Centurion Medical Products markets a commercially available catheter site dressing sold under the trademark Sorba-View® SHIELD. It was recognized that a one-step dressing for catheters would be very practical for dressing catheters. 3M Corporation markets a commercially available intravenous (IV) site transparent dressing sold under the trademark TEGADERM™-CHG (clorhexidine gluconate) that is claimed to reduce the incidence of catheter-related bloodstream infections (CRBSI), with the CHG being the antimicrobial agent. The CHG is embedded in a hydrogel pad. The gel pad does not have a slit to go around the device, so it can only be laid on top of the catheter. Thus, the device fails to provide 360 degree or complete circumferential coverage around the insertion site.

U.S. Pat. No. 5,833,665, issued Nov. 10, 1998 to Bootman, et al., is directed to a particular composition of a foam pad and shows a release profile of antimicrobial agent. This patent discloses a pad that is fully integrated or affixed to a top adhesive layer; both the pad and the adhesive layer are adapted with a slit. Positioning of this device over the insertion site of an indwelling catheter on a patient requires manipulation of the top layer and the pad, which could lead to catheter dislodgement or pistoning (moving back and forth), which might introduce bacteria into the bloodstream.

There is a need to provide an antimicrobial absorbent pad integrated with a transparent dressing, first to provide 360 degree protection of the catheter insertion site and for securing such pad, with an easy mechanism for deploying.

SUMMARY OF THE INVENTION

The present invention is directed to an integrated dressing for use with a percutaneous or drug delivery device, that has punctured the skin of a patient and that has a portion of the percutaneous medical device protruding from the skin. Examples of percutaneous devices are arterial or venous catheters, dialysis catheters, orthopedic pins, feeding tubes, wound drains, etc. The dressing of the present invention provides an integrated antimicrobial pad and a transparent dressing. The dressing has an easy mechanism for the health care practitioner dressing the insertion site to deploy both the antimicrobial pad and transparent dressing.

In one embodiment, the integrated dressing comprises a pad and an adhesive dressing. The pad has an upper surface, a skin or wound facing surface, a slit extending from an edge of the pad to a central point proximate to a center of the pad, and a bioactive agent. The wound in the present description refers to the catheter or percutaneous device penetration site on the skin. The adhesive dressing has a top side and a skin or wound facing side, the wound facing side having a layer of adhesive disposed thereon. There is a backing layer or liner that is attached to the adhesive side (wound facing side) of the transparent dressing, such backing layer or liner may or may not cover the upper surface of the antimicrobial pad. In one embodiment, the adhesive dressing is folded in half in a top side to top side orientation forming a fold line; the wound facing side of the adhesive dressing is divided into at least two portions by the fold line and each portion has a backing layer or liner attached thereto; and one of the liners attached to the wound facing side of the adhesive dressing comprises a cutout or notch at the fold line to allow partial clearance of the adhesive dressing. A portion of the upper surface of the pad not encompassing the slit is attached to the wound facing side of the adhesive dressing at the notch.

In another embodiment, the integrated dressing comprises a pad and an adhesive dressing. The pad has an upper surface, a skin or wound facing surface, a slit extending from the edge of the pad to a central point proximate to a center of the pad, and a bioactive agent. The adhesive dressing has a top side and a wound facing side, the wound facing side having a layer of adhesive disposed thereon. In this embodiment, the adhesive dressing is folded in half in a top side to top side orientation forming a first fold line; the wound facing side of the adhesive dressing is divided into at least two portions by the fold line and each portion has a liner attached thereto; the adhesive dressing is folded in half again in a wound facing side to wound facing side orientation forming a second fold line; and one of the liners attached to the wound facing side of the adhesive dressing comprises a cutout or notch at a central point where the first and second fold lines meet to allow partial clearance of the adhesive dressing. A portion of the upper surface of the pad not encompassing the slit is attached to the wound facing side of the adhesive dressing at the notch.

The bioactive agents suitable for use with the integrated dressings of the invention comprise one or more antimicrobial agents selected from the group consisting of chlorhexidine gluconate, chlorhexidine acetate, silver iodide, silver bromide, silver chloride, nano-particulate metallic silver, benzalkonium chloride, polyhexamethylene biguanide, Triclosan, metronidazole, alcohol, or iodine.

These and other objects of the present invention will be apparent from the following description, appended claims, and from practice of the invention.

BRIEF DESCRIPTION OF THE FIGURES

FIG. 4a illustrates the positioning of the slit of the pad over an indwelling catheter.

FIG. 4b illustrates the positioning of the dressing over the insertion site of the indwelling catheter on the patient.

FIG. 4c illustrates the pulling of the tab of the first liner to remove the first liner from the adhesive dressing, and the adherence of the portion of the adhesive dressing covered by the first liner to the skin of the patient.

FIG. 4d illustrates the pulling of the tab of the second liner to remove the second liner from the adhesive dressing, and the adherence of the portion of the adhesive dressing covered by the second liner to the skin of the patient.

FIG. 4e illustrates the fully deployed dressing device over an indwelling catheter on a patient.

DETAILED DESCRIPTION OF THE INVENTION

The device of the invention provides 360 degree coverage of the skin around insertion sites of percutaneous devices and comprises a pad for wicking away blood and exudates and an adhesive dressing for securing the pad to the skin of a patient.

It is an object of the invention to provide an integrated dressing that is easily applied around insertion sites of percutaneous devices, and may also, if necessary, serve as a delivery vehicle for release of a bioactive agent entirely around a wound or insertion site of a percutaneous or drug delivery device. The device of the invention is easy to deploy and position, thus saving time for the healthcare professional. Specifically, the device of the invention minimizes the steps required for deploying the dressing with the convenience of opening just one package in a sterile environment, as opposed to having to open a package containing an antimicrobial pad and a package containing an adhesive dressing.

Deploying the device of the invention, or dressing an insertion site of a percutaneous device, involves placing an antimicrobial pad around the insertion site and immediately deploying the transparent dressing without the healthcare professional having to remove their hand from the device. The transparent dressing integrated with the antimicrobial pad, provides an easy way to situate the pad containing the antimicrobial in such a way that the antimicrobial side is always facing the skin around the insertion site. The device of the invention can possibly be manufactured using a high speed web converting process that automates the attachment of the antimicrobial pad to the transparent dressing.

The inventors discovered that folding the adhesive dressing on itself at least once provided for an unexpectedly convenient way of installing the antimicrobial pad and transparent dressing over the catheter with easy access to the catheter without the antimicrobial pad being in the way or dislodging the catheter. Furthermore, the inventors discovered that after positioning the antimicrobial pad over the catheter, it was easy to deploy the adhesive dressing by unfolding and removing the liners, optionally from each folded section separately.

These and other objects of the invention will be apparent from the following description and appended claims and from practice of the invention. It is to be understood that the figures discussed in the following description are for illustrative purposes only to show the relationship of the elements of the dressing device and not necessarily drawn to scale.

Figure 1A:
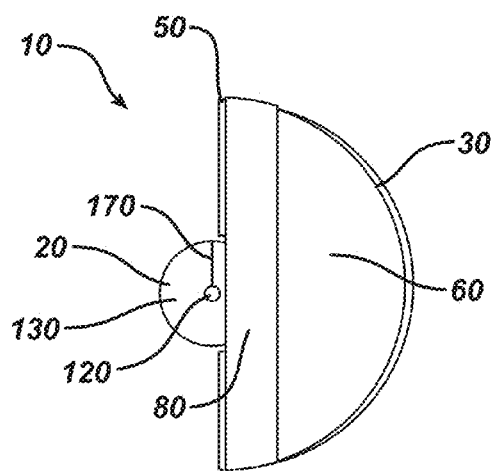
FIG. 1a illustrates a perspective view of a dressing device of the invention, specifically the upper surface of a pad showing an aperture proximate to a center of the pad wherein a portion of the upper surface of the pad is adhesively attached to the wound facing side of an adhesive dressing at the notch (not shown), the adhesive dressing folded in half in a top side to top side orientation forming a fold line, and a first liner attached to the wound facing side of the adhesive dressing, wherein the first liner comprises a tab.

Referring to FIG. 1a, illustrated is a perspective view of a dressing device 10 of the invention comprising a pad 20 and an adhesive dressing 30. The pad 20 has an upper surface 130 (shown in FIG. 1a), a wound facing surface (not shown) opposing the upper surface, and a bioactive agent, which is disposed on the wound facing surface or impregnated throughout the pad 20. The pad 20 also comprises a slit 170 extending from an edge of the pad 20 to an aperture 120 positioned substantially in or proximate to the center of the pad 20 so that the pad 20 of the dressing device 10 can be deployed over an already placed catheter.

The adhesive dressing 30 has a top side and a wound facing side (shown in FIG. 1*a*), wherein the wound facing side has a layer of adhesive disposed thereon. FIG. 1*a* illustrates that the adhesive dressing 30 is folded in half in a top side to top side orientation forming a fold line 50. The wound facing side of the adhesive dressing 30 is divided into at least two portions by the fold line 50 and each portion has a disposable removable protective liner attached thereto. FIG. 1*a* illustrates that a first portion of the adhesive dressing 30 has a first liner 60 comprising a first tab 80 for removing the first liner 60 from the adhesive dressing 30.

Figure 1B:
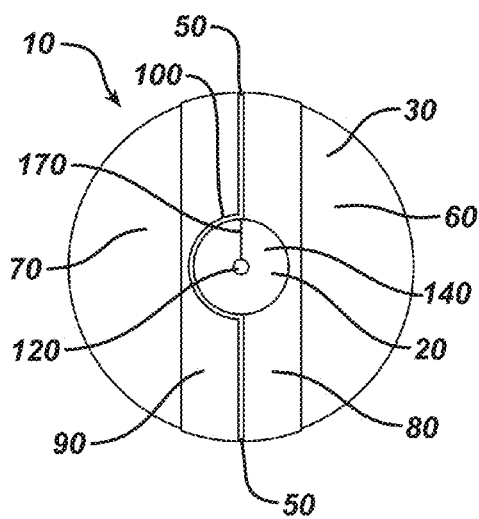
FIG. 1b illustrates the wound facing side of a dressing device of the invention shown in FIG. 1a, wherein the dressing device is unfolded and comprises a pad (wound facing side shown with an aperture proximate to a center of the pad) adhesively attached to the wound facing side of the adhesive dressing at the cutout or notch, the adhesive dressing divided into two portions by a fold line and comprising first and second liners with tabs.

Referring now also to FIG. 1*b*, the second liner 70 (not shown in FIG. 1*a*) is attached to a second portion the adhesive dressing 30 having a cutout or notch 100 (not shown in FIG. 1*a*) at the fold line 50 thereby exposing a portion or area 105 of the layer of adhesive (not shown in FIG. 1*a* or 1*b*) disposed on the second portion of the adhesive dressing 30, wherein a portion of the upper surface of the antimicrobial pad 20 not encompassing the slit 170 is adhesively attached to the wound facing side of the adhesive dressing 30 at the notch 100. Specifically, a portion of the upper surface of the antimicrobial pad 20 not encompassing the slit 170 is adhesively attached to the wound facing side of the adhesive dressing 30 on the portion of the layer adhesive (disposed on the second portion of the adhesive dressing 30) that is exposed by the notch or cutout 100.

FIG. 1*b* illustrates the wound facing side of a dressing device 10 of the invention shown in FIG. 1*a*. In FIG. 1*b*, the dressing device 10 is unfolded and comprises a pad 20 and an adhesive dressing 30. The pad 20 has an upper surface, a wound facing surface 140, and a bioactive agent, which is disposed on the wound facing surface 140 or impregnated throughout the pad 20. The pad 20 also comprises a slit 170 extending from an edge of the pad 20 to an aperture 120 positioned substantially in or proximate to the center of the pad 20. The adhesive dressing 30 is divided into two portions by the fold line 50 and comprises first 60 and second 70 liners with first 80 and second 90 tabs for removing the first 60 and second 70 liners from the adhesive dressing 30. The second liner 70 attached to a second portion the adhesive dressing 30 comprises a notch 100 at the fold line 50 thereby exposing a portion or area 105 of the layer of adhesive (not shown in FIG. 1*b*) disposed on the second portion of the adhesive dressing 30. The pad 20 is adhesively attached to the second portion of the wound facing side (shown in FIG. 1*b*) of the adhesive dressing 30 at the notch 100 of the second liner 70. Specifically, a portion of the upper surface of the antimicrobial pad 20 not encompassing the slit 170 is adhesively attached to the wound facing side of the adhesive dressing 30 on the portion of the layer adhesive (disposed on the second portion of the adhesive dressing 30) that is exposed by the notch 100.

Figure 1C:
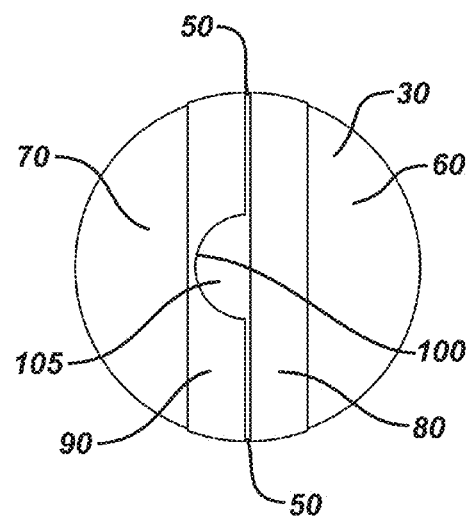
FIG. 1c illustrates a portion of the wound facing side of a dressing device of the invention shown in FIG. 1a, wherein the dressing device is unfolded and shown without the pad, thereby showing the adhesive area exposed by the notch.

FIG. 1*c* shows the wound facing side of a dressing device 10 of the invention shown in FIGS. 1*a*-1*b*, with the pad 20 removed. The second liner 70 attached to a second portion the adhesive dressing 30 comprises a notch 100 at the fold line 50 thereby exposing an adhesive area which comprises a portion or area 105 of the layer of adhesive disposed on the second portion of the adhesive dressing 30. The pad 20 is adhesively attached at the exposed adhesive area 105 to the second portion of the wound facing side of the adhesive dressing 30 at the notch 100 of the second liner 70. Specifically, a portion of the upper surface of the antimicrobial pad 20 not encompassing the slit 170 is adhesively attached to the wound facing side of the adhesive dressing 30 in the exposed adhesive area 105 on the portion of the layer adhesive (disposed on the second portion of the adhesive dressing 30) that is exposed by the notch 100.

Figure 2:
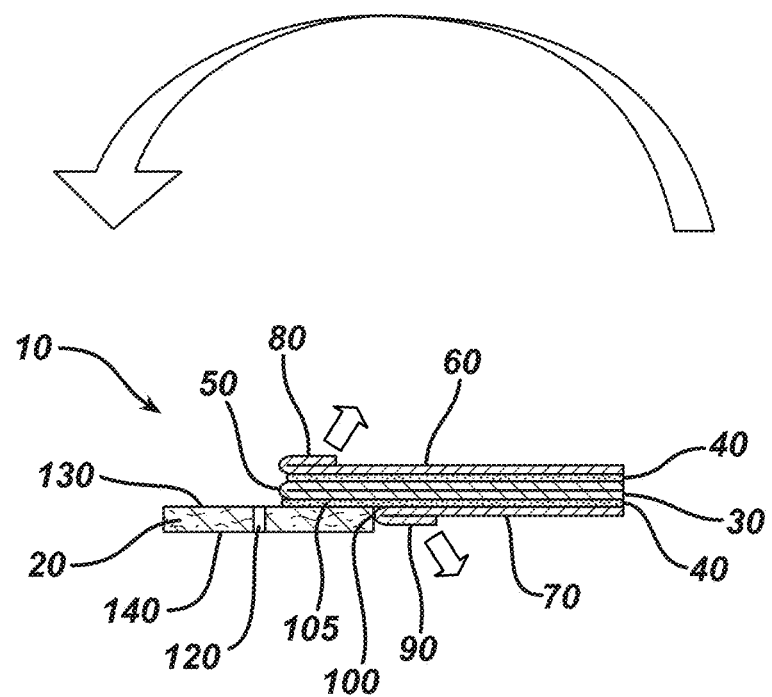
FIG. 2 illustrates a cross section view of a dressing device of the invention like that shown in FIGS. 1a and 1b, wherein the dressing device is in the folded position prior to deployment.

FIG. 2 illustrates a cross section view of a dressing device 10 of the invention like that shown in FIG. 1*a*, wherein the dressing device 10 is in the folded position prior to deployment. Specifically, the dressing device 10 illustrated in FIG. 2 comprises a pad 20 having an upper surface 130, a wound facing surface 140, a slit (not shown) extending from an edge of the pad 20 to an aperture 120 positioned substantially in or proximate to the center of the pad 20, and a bioactive agent, which is disposed on the wound facing surface 140 or impregnated throughout the pad 20. The dressing device 10 further comprises an adhesive dressing 30 having a top side and a wound facing side, the wound facing side having a layer of adhesive 40 disposed thereon, wherein the adhesive dressing 30 is folded in half in a top side to top side orientation forming a fold line 50.

The wound facing side of the adhesive dressing 30 shown in FIG. 2 is divided into at least two portions by the fold line 50 and each portion has a liner attached thereto. In FIG. 2, a first portion of the adhesive dressing 30 has a first liner 60 comprising a first tab 80 for removing the first liner 60 from the adhesive dressing 30, and a second portion of the adhesive dressing 30 has a second liner 70 comprising a second tab 90 for removing the second liner 70 from the adhesive dressing 30. The arrows shown in FIG. 2 at the first 80 and second 90 tabs illustrate the direction in which the tabs are to be pulled in order to remove the first 60 and second 70 liners from the first and second portions of the adhesive dressing 30. The second liner 70 of the second portion of the adhesive dressing 30 comprises a notch 100 at the fold line 50 thereby exposing a portion or area 105 on the layer of adhesive 40 disposed on the second portion of the adhesive dressing 30, and a portion of the upper surface of the antimicrobial pad 20 not encompassing the slit is adhesively attached to the wound facing side of the adhesive dressing 30 at the notch 100. Specifically, a portion of the upper surface of the antimicrobial pad 20 not encompassing the slit 170 is adhesively attached to the wound facing side of the adhesive dressing 30 on the adhesive portion or area 105 (disposed on the second portion of the adhesive dressing 30) that is exposed by the notch 100. The arrow at the top of FIG. 2 illustrates the direction in which the first portion of the adhesive dressing 30 with a first liner 60 is to be deployed over a wound or insertion site of percutaneous or drug delivery device.

Figure 3:
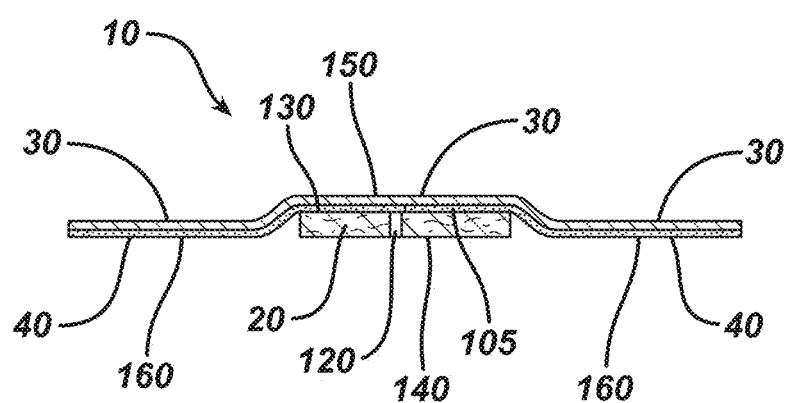
FIG. 3 illustrates a cross section view of a dressing device of the invention like that shown in FIGS. 1a and 1b, wherein the dressing device is deployed over an insertion site of a percutaneous or drug delivery device.

FIG. 3 illustrates a cross section view of a dressing device 10 of the invention like that shown in FIGS. 1*a* and 1*b*, wherein the dressing device 10 is deployed over an insertion site of a percutaneous or drug delivery device (not shown). Specifically, the dressing device 10 illustrated in FIG. 3 comprises a pad 20 having an upper surface 130, a wound facing surface 140, a slit (not shown) extending from an edge of the pad 20 to an aperture 120 positioned substantially in or proximate to the center of the pad 20, and a bioactive agent, which is disposed on the wound facing surface 140 or impregnated throughout the pad 20. The dressing device 10 further comprises an adhesive dressing 30 having a top side 150 and a wound facing side 160, the wound facing side 160 having a layer of adhesive 40 disposed thereon. FIG. 3 also illustrates where a portion of the upper surface of the antimicrobial pad 20 not encompassing the slit was adhesively attached in the adhesive portion or area 105 defined by the notch 100 (not shown) to the wound facing side of the adhesive dressing 30 prior to deployment of the dressing device 10.

The pad 20 and the adhesive dressing 30 of the dressing device 10 illustrated in FIGS. 1-3 may be of any suitable shape. In one embodiment, the pad 20 of the dressing device 10 illustrated in FIGS. 1-3 has a circular shape and the notch 100 is rounded or semi-circular to match the shape of the pad 20. For different shapes of the pad 20, the notch 100 will have a complementary shape to define the adhesive area 105 by exposing a portion of the adhesive disposed on the second portion of the adhesive dressing 30. There needs to be circumferential coverage around the insertion site of a percutaneous device, but the pad 20 itself could be any other suitable shape. In another embodiment, the notch 100 is located at the fold line 50 at a center of the adhesive dressing. The pad 20 could be attached at a notch 100 located on the second liner 70 of the second portion of the adhesive dressing 30 elsewhere on the fold line 50 of the adhesive dressing 30 as long as a portion 105 of the layer of adhesive disposed on the second portion of the adhesive dressing 30 is exposed enough to allow for secure adherence of the pad 20 to the adhesive dressing 30 and also to allow manipulation of the pad 20 around the insertion site of an indwelling catheter and ensure circumferential adherence of the pad 20 around the insertion site.

In one embodiment, the adhesive dressing 30 has a circular shape. Other suitable shapes include, but are not limited to rectangular, oval, trapezoidal, or any polygonal shape, with the design adapted so that the shape of the notch 100 closely matches the shape of the pad 20. The gaps between the pad 20 and the liners 60 and 70 are from about 0.1 mm to about 2 mm, such as from 0.25 mm to 0.5 mm. One skilled in the art would understand how to modify the shape and size, including the length, of the devices of the invention based on one's anticipated outcome, including but not limited to, intended use of the device and intended dosage and release profile of a bioactive agent(s).

In yet another embodiment, the adhesive dressing 30 is at least partially transparent (with the light transmission from about 25 percent to about 100 percent, such as from 50 percent to about 99 percent) allowing a healthcare professional to visually check on a wound or the area of skin around the insertion site of a percutaneous or drug delivery device, such as a catheter. In another embodiment, half of the upper surface 130 of the antimicrobial pad 20 not encompassing the slit is adhesively attached to the wound facing side 160 of the adhesive dressing 30 at the notch 100. Specifically, half of the upper surface of the antimicrobial pad 20 not encompassing the slit 170 is adhesively attached to the wound facing side of the adhesive dressing 30 on the portion 105 of the layer of adhesive (disposed on the second portion of the adhesive dressing 30) that is exposed by the notch 100. Up to half of the upper surface 130 of the antimicrobial pad 20 not encompassing the slit can be adhesively attached to the wound facing side 160 of the adhesive dressing 30 as long as the slit is exposed to allow for manipulation of the pad 20 around the insertion site of an indwelling catheter or other percutaneous medical device and the pad 20 and adhesive dressing 30 are attached enough to ensure that dressing device 10 is an integrated device as described herein.

Figure 5A:
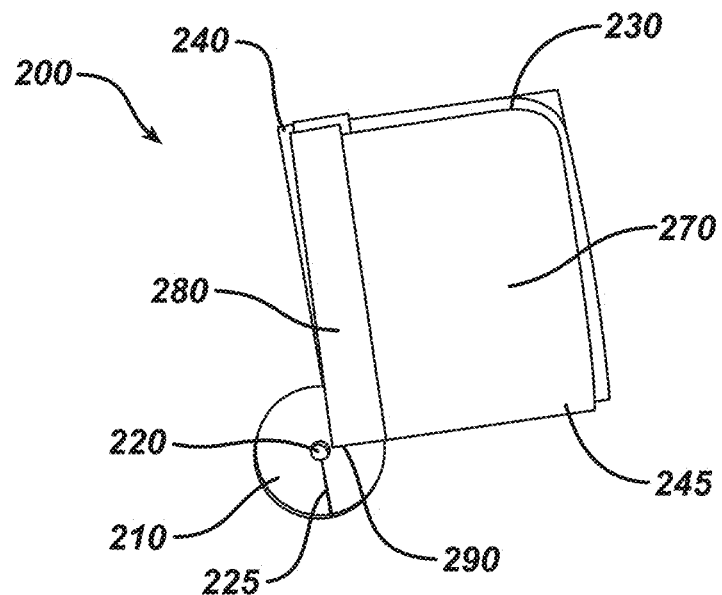
FIG. 5a illustrates an alternative embodiment of a dressing device of the invention, specifically the upper surface of a pad showing an aperture proximate to a center of the pad wherein a portion of the upper surface of the pad is adhesively attached to the wound facing side of an adhesive dressing at the notch (not shown), the adhesive dressing folded in half two times forming a central portion where two fold lines meet, and a second liner attached to the wound facing side of the adhesive dressing, wherein the second liner comprises a tab. The wound facing side of the adhesive dressing liner is shown in this figure.

In FIG. 5a, another embodiment of the dressing device 200 according to the invention is shown. The embodiment illustrated in FIG. 5a comprises a pad 210 having an upper surface (shown in FIG. 5a), a wound facing surface (not shown in FIG. 5a), a slit 225 extending from the edge of the pad 210 to an aperture 220 positioned substantially in or proximate to the center of the pad 210, and a bioactive agent which is disposed on the wound facing surface or impregnated throughout the pad 210. The embodiment illustrated in FIG. 5a further comprises an adhesive dressing 230 having a top side and a wound facing side (shown in FIG. 5a), the wound facing side having a layer of adhesive disposed thereon.

FIG. 5a illustrates that the adhesive dressing 230 is folded in half in a top side to top side orientation forming a first fold line 240. The wound facing side of the adhesive dressing 230 is divided into at least two portions by the first fold line 240 and each portion has a disposable removable protective liner attached thereto. The adhesive dressing 230 is folded in half again in a wound facing side to wound facing side orientation forming a second fold line 245. FIG. 5a illustrates that a second portion of the adhesive dressing 230 has a second liner 270 comprising a second tab 280 for removing the second liner 270 from the adhesive dressing 230. The second liner 270 attached to a second portion of the adhesive dressing 230 comprises a notch (not shown in FIG. 5a) at a central point 290 where the first 240 and second 245 fold lines meet thereby exposing a portion of the layer of adhesive disposed on the second portion of the adhesive dressing 230. In the embodiment illustrated in FIG. 5a, a portion of the upper surface of the antimicrobial pad 210 not encompassing the slit 225 is adhesively attached to the wound facing side of the adhesive dressing 230 at the notch. Specifically, a portion of the upper surface of the antimicrobial pad 210 not encompassing the slit 225 is adhesively attached to the wound facing side of the adhesive dressing 230 on the portion of the layer adhesive (disposed on the second portion of the adhesive dressing 230) that is exposed by the notch.

Figure 5B:
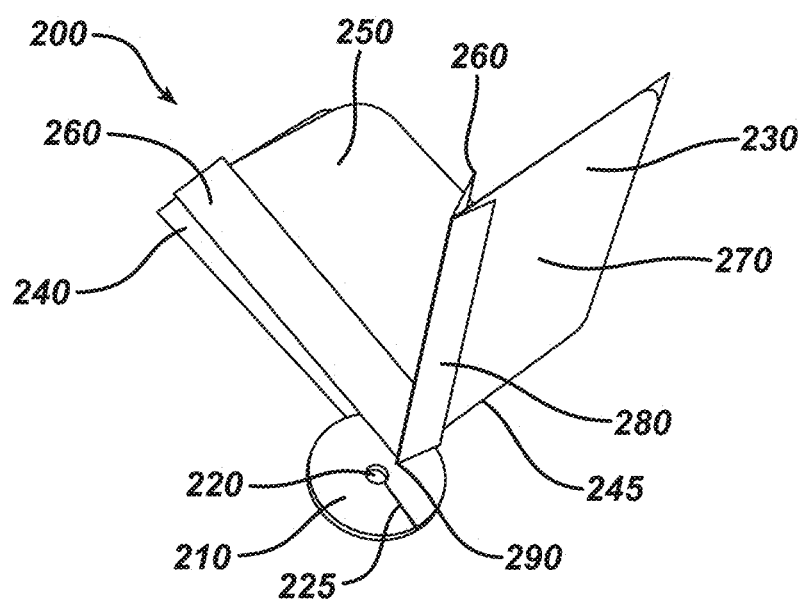
FIG. 5b illustrates an alternative view of the embodiment of a dressing device of the invention shown in FIG. 5a, specifically the upper surface of a pad showing an aperture proximate to a center of the pad wherein a portion of the upper surface of the pad is adhesively attached to the wound facing side of the adhesive dressing at the notch (not shown), the adhesive dressing folded in half two times forming a central portion at a fold line, and a first and second liner attached to the wound facing side of the adhesive dressing, wherein the first and second liners each comprise a tab.

In FIG. 5b, another view of the embodiment of the dressing device 200 according to the invention illustrated in FIG. 5a is shown. The embodiment illustrated in FIG. 5b comprises a pad 210 having an upper surface (shown in FIG. 5b), a wound facing surface opposite the upper surface, a slit 225 extending from the edge of the pad 210 to an aperture 220 positioned substantially in or proximate to the center of the pad 210, and a bioactive agent which is disposed on the wound facing surface or impregnated throughout the pad 210. The embodiment illustrated in FIG. 5b further comprises an adhesive dressing 230 having a top side and a wound facing side (shown in FIG. 5b), the wound facing side having a layer of adhesive disposed thereon.

FIG. 5b illustrates that the adhesive dressing 230 is folded in half in a top side to top side orientation forming a first fold line 240. The wound facing side of the adhesive dressing 230 is divided into at least two portions by the first fold line 240 and each portion has a liner disposable removable protective liner attached thereto. The adhesive dressing 230 is folded in half a second time, this time in a wound facing side to wound facing side orientation forming a second fold line 245. FIG. 5b illustrates a second portion of the adhesive dressing 230 having a second liner 270 comprising a second tab 280 for removing the second liner 270 from the adhesive dressing 230 and a first portion of the adhesive dressing 230 having a first liner 250 comprising a first tab 260 for removing the first liner 250 from the adhesive dressing 230. The second liner 270 attached to a second portion of the adhesive dressing 230 comprises a notch or cutout in the liner 270 (not shown in FIG. 5b) at a central point 290 where the first 240 and second 245 fold lines meet thereby exposing a portion of the layer of adhesive disposed on the second portion of the adhesive dressing 230. In the embodiment illustrated in FIG. 5b, a portion of the upper surface of the antimicrobial pad 210 not encompassing the slit 225 is adhesively attached to the wound facing side of the adhesive dressing 230 at the notch. Specifically, a portion of the upper surface of the antimicrobial pad 210 not encompassing the slit 225 is adhesively attached to the wound facing side of the adhesive dressing 230 on the portion of the layer adhesive (disposed on the second portion of the adhesive dressing 230) that is exposed by the notch.

The pad 210 and the adhesive dressing 230 of the dressing device 200 illustrated in FIGS. 5a and 5b may be of any suitable shape. In one embodiment, the pad 210 of the dressing device 200 illustrated in FIGS. 5a and 5b has a circular shape and the notch has a shape corresponding to the projection onto the dressing of the portion of the pad 210 attached to the adhesive dressing 230. There needs to be circumferential coverage around the insertion site of a percutaneous device (not shown), but the pad 210 could be of any other suitable shape. In another embodiment, the notch is located at a central point 290 where the first 240 and second 245 fold lines meet. The pad 210 could be attached at a notch located elsewhere on the second liner 270 of the second portion of the adhesive dressing 230 on the first 240 or second 245 fold lines of the adhesive dressing 230 as long as a portion of the layer of adhesive disposed on the second portion of the adhesive dressing 230 is exposed enough to allow for secure adherence of the pad 210 to the adhesive dressing 230 and also to allow manipulation of the pad 210 around the insertion site of an indwelling catheter and ensure circumferential adherence of the pad 210 around the insertion site.

In yet another embodiment, the adhesive dressing 230 has rounded corners. Other suitable shapes of the adhesive dressing 230 include, but are not limited to, round, square, rectangular, elliptical, trapezoidal, or any other suitable shape that ensures complete coverage of the pad and reliable adherence to skin. In one embodiment, a size of the adhesive dressing 230 is from about 3 cm squared to about 600 cm squared. One skilled in the art would understand how to modify the shape and size, including the length, of the devices of the invention based on one's anticipated outcome, including but not limited to, intended use of the device and intended dosage and release profile of a bioactive agent(s).

In yet another embodiment, the adhesive dressing 230 is at least partially transparent (with the light transmission from about 25 percent to about 100 percent, such as from 50 percent to about 99 percent), allowing a healthcare professional to visually check on a wound or the area of skin around the insertion site of a percutaneous or drug delivery device, such as a catheter. In another embodiment, a quarter of the upper surface of the antimicrobial pad 210 not encompassing the slit 225 is adhesively attached to the wound facing side of the adhesive dressing 230 at the notch. Specifically, a quarter of the upper surface of the antimicrobial pad 210 not encompassing the slit 225 is adhesively attached to the wound facing side of the adhesive dressing 230 on the portion of the layer adhesive (disposed on the second portion of the adhesive dressing 230) that is exposed by the notch. In another embodiment, up to one half of the upper surface of the antimicrobial pad 210 not encompassing the slit 225 is adhesively attached to the wound facing side of the adhesive dressing 230.

The embodiments illustrated in FIGS. 1-5 are adapted for use with a percutaneous or drug delivery medical device that has punctured the skin of a patient and has a portion of the percutaneous or drug delivery medical device protruding from the skin by further comprising a slit as discussed above. Specifically, the pads 20 and 210 of the dressing devices 10 and 200 illustrated in FIGS. 1-5 have slits that can be formed by cutting, punching, or similar. The widths of slits 170 and 225 of the pads illustrated in FIGS. 1-5 are adapted to facilitate installation over the already installed indwelling catheter. The width of slits range from very small when the sides of the slit touch each other (i.e. a cut with a very narrow blade), corresponding to a slit from about zero gap to about 1 mm gap, or from zero to about 50 microns gap. The slits enable the dressing devices of the invention to fully surround the catheter at the insertion or puncture site. The size of the aperture 120 and 220 is adapted for fully surrounding the percutaneous or drug delivery medical device or catheter protruding from the skin in a snug or loose configuration, with the diameter of the aperture ranging from about 90 percent of the outside diameter of the percutaneous catheter to about 150 percent of the outside diameter of the percutaneous catheter, such as 95 percent, 102 percent, 105 percent, or 110 percent of the outside diameter of the percutaneous catheter. In one embodiment, the aperture diameter is equal to 100 percent of the outside diameter of the percutaneous catheter.

Materials

The pad 20 of dressing device 10 and the pad 210 of dressing device 200 may be formed from a pad impregnated with an antimicrobial agent, such as the commercially available pad product sold under the trade mark BIOPATCH® marketed by Johnson & Johnson Corporation. BIOPATCH® is applied around percutaneous devices to prevent localized infection at the insertion site and is a foam material that contains the antimicrobial agent chlorhexidine gluconate (CHG). Other suitable materials for pads 20 and 210 include any tissue compatible absorbent foam, hydrogel, fabric, woven or non-woven material, cellulose-based material, or fiber structure or other suitable material. The absorbent material may comprise a felt, such as polyurethane foam; polyester mats, such as DACRON® polyester fiber mats that are commercially available from DuPont, Inc.; natural, synthetic, or hybrid synthetic/natural polyester; cellulose; alginate; polyacrylates; polyolefins; and cottons.

The bioactive agent that can be incorporated in the pad 20 and 210 can be an antimicrobial agent such as a chlorhexidine compound, for instance chlorhexidine gluconate or chlorhexidine acetate; silver compounds, for instance silver iodide, silver bromide, silver chloride, or nano-particulate metallic silver; benzalkonium chloride; polyhexamethylene biguanide (PHMB); triclosan; antibiotics such as metronidazole; alcohol; iodine; or other known antimicrobial compounds and combinations thereof that are compatible with skin and useful against a range of microorganisms, for example against known skin flora such as *Staphylococcus aureus* and methicillin-resistant *Staphylococcus aureus* (MRSA). In one embodiment, the bioactive agent is chlorhexidine gluconate, an agent known to be safe and effective and widely used as a surgical disinfectant. Plasticizers, colorants, surfactants, and stabilizers, singular or in combination, can also be incorporated in the pad 20 and 210.

As previously discussed, the pads 20 and 210 shown in FIGS. 1-5 may be of any suitable shape. The diameter and thickness of the pad 20 and 210 may be varied as desired, depending upon the desired pharmaceutical dosage and duration of delivery. Ordinarily, a suitable pad diameter will be in a range of about 1 cm to about 10 cm, such as from 2 cm to about 5 cm, or about 2.5 cm. A suitable pad thickness will be in a range of about 1 mm to about 5 mm such as 2 mm to 3 mm. The diameter of the aperture 120 and 220 in the embodiments discussed above is selected so as to accommodate the appropriate catheter snugly, in tight engagement, with typical diameters ranging from 1 mm to about 20 mm, such as from 1 mm to 15 mm.

The adhesive dressing 30 of dressing device 10 and the adhesive dressing 230 of dressing device 200 can be formed from any adhesive transparent dressing for wounds, such as BIOCLUSIVE® transparent dressing marketed by Systagenix Wound Management Ltd. Other suitable materials for adhesive dressings 30 and 230 include transparent polyester films with pressure sensitive biocompatible adhesive. The adhesive dressings 30 and 230 have a continuous layer of adhesive disposed thereon, typically a pressure sensitive adhesive layer. The pressure-sensitive adhesive can be any pressure sensitive adhesive known in the art. The adhesive layer typically has a thickness from about 5-10 microns to about 200-500 microns. The adhesive can also be discontinuous, i.e. applied in a patterned fashion. In one embodiment, the adhesive is applied in stripes, thus providing for breathability of the dressing.

As previously discussed, the adhesive dressings 30 and 230 shown in FIGS. 1-5 may be of any suitable shape. In one embodiment, the adhesive dressing 30 is circular with a diameter of at least twice the diameter of the pad 20 or 210, such as from two times to five times the diameter of the pad 20 or 210, such as from 2 cm to 20 cm. In one embodiment, the size of the adhesive dressings 30 and 230 is three quarters of an inch outside diameter; 1.5 inch outside diameter; or two inches outside diameter.

The diameter of the apertures 120 and 220 range from 1.0 mm to 7 mm (inside diameter) and up to 14 mm. In one embodiment, the diameter of the dressing device 10 illustrated in FIGS. 1-5 can range from 5 to 15 cm with a ratio of diameters of the adhesive dressing to pad at approximately two to four.

In another embodiment, the adhesive dressing 230 is created by cutting out a 4 inch by 5 inch rectangular section from the center of a 5 inch by 7 inch transparent dressing with disposable removable protective liners (paper backing) attached thereto (such as BIOCLUSIVE® Transparent Dressing). The corners can then be rounded to prevent peel-up.

The notches of the adhesive dressings 30 and 230 can be cut out of the second liners 70 and 270 for attachment of the pads 20 and 210 to the adhesive dressings 30 and 230 by using a circular punch, laser cutting, or any other suitable cutting method. The notches allow adherence of a portion of the upper surface of the antimicrobial pad 20 or 210 not encompassing the slit to adhesively attach to the wound facing side of the adhesive dressing 30 or 230 at the notch. Specifically, a portion of the upper surface of the antimicrobial pad 20 or 210 not encompassing the slit is adhesively attached to the wound facing side of the adhesive dressing 30 or 230 on the portion (105 in FIGS. 1c, 2, and 3) of the layer adhesive (disposed on the second portion of the adhesive dressing 30 or 230) that is exposed by the notch.

Percutaneous Medical Devices

Percutaneous medical devices for which the dressing devices of the present invention can be used include catheters, pins, implants, and the like which pass through the skin and are indwelling for some considerable time. Exemplary of percutaneous medical devices are central venous catheters, peripheral venous catheters, Swan-Ganz pulmonary catheters, central nervous system implants, such as external ventricular drainage and ventricular reservoirs, peritoneal dialysis catheters, such as for continuous ambulatory peritoneal dialysis and continuous cyclic peritoneal dialysis, hemodialysis catheters, transvenous pacemaker leads, and temporary orthopedic pins. All of these percutaneous medical devices, when in place, have a portion of the device that is external and left protruding from the skin, which can be the cause of infection around the insertion sites of the medical devices.

Method

Figure 4A:
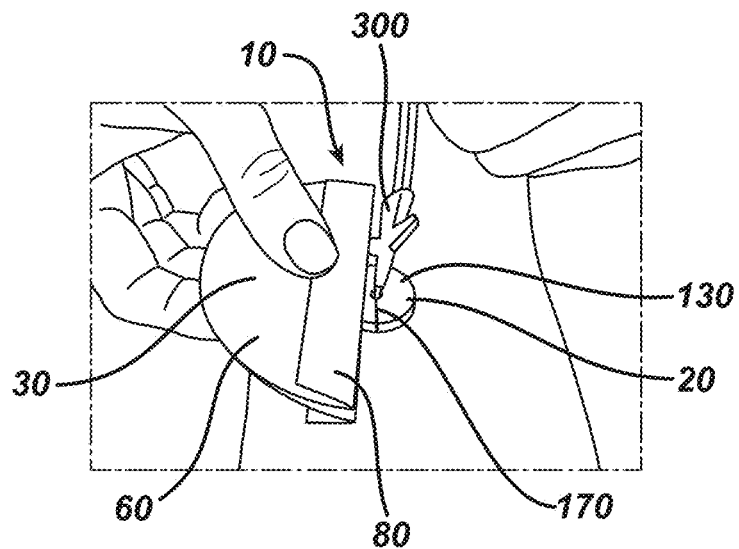
FIGS. 4a through 4e illustrate the steps involved in the deployment of a dressing device shown in FIGS. 1-3 over an indwelling catheter.

The present invention also relates to a method of dressing the wound site or the insertion site of a percutaneous or drug delivery medical device for a patient using such a device. FIGS. 4a through 4e illustrate the steps involved in the deployment of a dressing device 10 shown in FIGS. 1-3 over an indwelling catheter. As shown in FIG. 4a, when used over a percutaneous or drug delivery medical device, the dressing device 10 is applied by positioning the slit 170 of the pad 20 over an indwelling catheter 300. The indwelling catheter is guided through the slit 170, enabling the pad 20 to fully surround the catheter at the insertion or puncture site. The wound facing surface opposite the upper surface 130 of the pad 20 comprising a bioactive agent is thereby in contact with the skin surrounding the puncture site. The dressing device 10 provides 360 degree or complete circumferential coverage around the catheter shaft. FIG. 4a also shows the first liner 60 comprising the first tab 80 of the adhesive dressing 30 and the upper surface 130 of the pad 20.

Figure 4B:
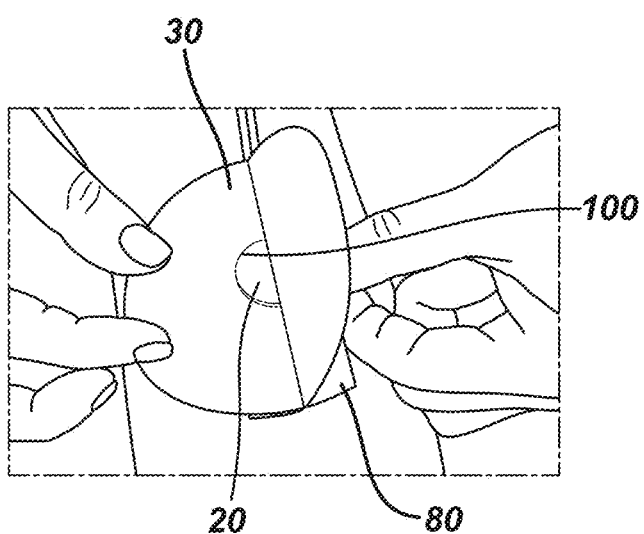

FIG. 4b illustrates the positioning of the adhesive dressing 30 over the insertion site of the indwelling catheter (not visible in FIG. 4b) surrounded by the pad 20 on the patient. FIG. 4b also illustrates the notch 100 wherein a portion of the upper surface of the antimicrobial pad 20 not encompassing the slit is adhesively attached to the wound facing side of the adhesive dressing 30 at the notch 100.

Figure 4C:
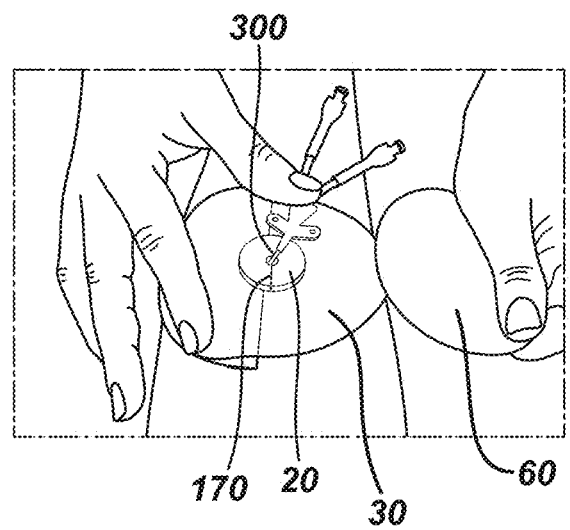

FIG. 4c illustrates the pulling of the first tab 80 (visible in FIGS. 4a and 4b) of the first liner 60 to remove the first liner 60 from the adhesive dressing 30, and the adherence of the portion of the adhesive dressing 30 comprising the first liner 60 to the skin of the patient.

Figure 4D:
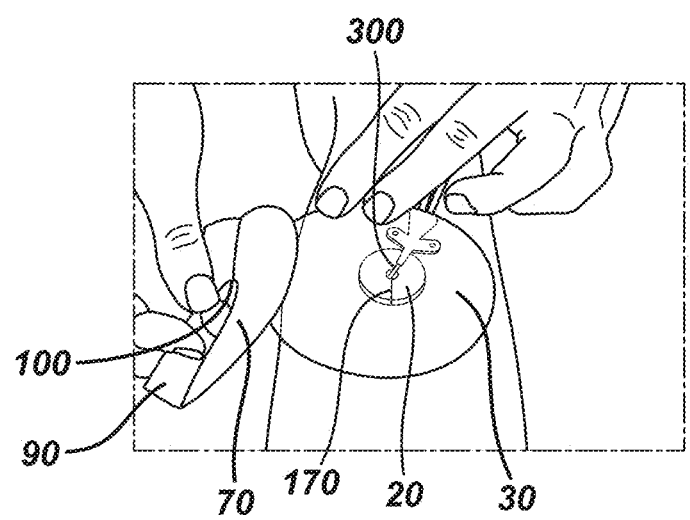
Figure 4E:
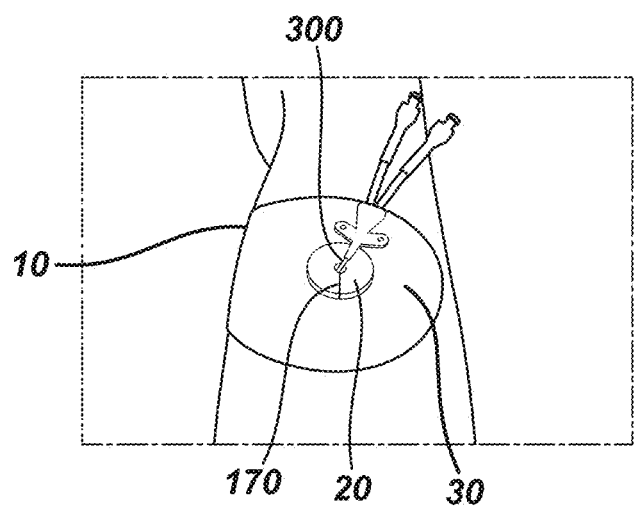

FIG. 4d illustrates the pulling of the second tab 90 of the second liner 70 (comprising a notch 100) to remove the second liner 70 from the adhesive dressing 30, and the adherence of the portion of the adhesive dressing 30 comprising the second liner 70 to the skin of the patient. FIG. 4e illustrates the fully deployed dressing device 10 comprising a pad 20 and an adhesive dressing 30 over an indwelling catheter 300 on a patient.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

We claim:

1. An integrated dressing device comprising:
  a pad having an upper surface, a wound facing surface, a slit extending from an edge of the pad to an aperture proximate to a center of the pad, and a bioactive agent;
  an adhesive dressing having a top side and a wound facing side, the wound facing side having a layer of adhesive disposed thereon;
  wherein the adhesive dressing is folded in half in a top side to top side orientation forming a fold line;
  wherein the wound facing side of the adhesive dressing is divided into at least two portions by the fold line and each portion has a liner attached thereto;
  wherein one of the liners attached to the wound facing side of the adhesive dressing comprises a notch at the fold line thereby exposing an area of the layer of adhesive disposed on the adhesive dressing; and
  wherein a portion of the upper surface of the pad not encompassing the slit is attached to the wound facing side of the adhesive dressing at the area of the layer of adhesive disposed on the adhesive dressing exposed by the notch.

2. The dressing device according to claim 1, wherein the bioactive agent is an antimicrobial agent.

3. The dressing device according to claim 2, wherein the bioactive agent comprises one or more antimicrobial agents selected from the group consisting of chlorhexidine gluconate, chlorhexidine acetate, silver iodide, silver bromide, silver chloride, nano-particulate metallic silver, benzalkonium chloride, polyhexamethylene biguanide, Triclosan, metronidazole, alcohol, or iodine.

4. The dressing device of claim 2, wherein the bioactive agent is chlorhexidine gluconate.

5. The dressing device of claim 1, wherein the adhesive dressing has a circular shape.

6. The dressing device of claim 1, wherein the pad has a circular shape.

7. The dressing device of claim 6, wherein the notch is rounded.

8. The dressing device of claim 1, wherein the notch is located at the fold line at a center of the adhesive dressing.

9. The dressing device of claim 1, wherein the adhesive dressing is at least partially transparent.

10. The dressing device of claim 1, wherein half of the upper surface of the pad not encompassing the slit is attached to the wound facing side of the adhesive dressing at the area of the layer of adhesive disposed on the adhesive dressing exposed by the notch.

11. The dressing device of claim 5, wherein a diameter of the adhesive dressing is from about 2 cm to about 30 cm.

12. The dressing device of claim 1, wherein the liners each comprise a tab.

13. An integrated dressing device comprising:
a pad having an upper surface, a wound facing surface, a slit extending from an edge of the pad to an aperture proximate to a center of the pad, and a bioactive agent;
an adhesive dressing having a top side and a wound facing side, the wound facing side having a layer of adhesive disposed thereon;
wherein the adhesive dressing is folded in half in a top side to top side orientation forming a first fold line;
wherein the wound facing side of the adhesive dressing is divided into at least two portions by the first fold line and each portion has a liner attached thereto;
wherein the adhesive dressing is folded in half again in a wound facing side to wound facing side orientation forming a second fold line;
wherein one of the liners attached to the wound facing side of the adhesive dressing comprises a notch at a central point where the first and second fold lines meet thereby exposing an area of the layer of adhesive disposed on the adhesive dressing; and
wherein a portion of the upper surface of the pad not encompassing the slit is attached to the wound facing side of the adhesive dressing at the area of the layer of adhesive disposed on the adhesive dressing exposed by the notch.

14. The dressing device according to claim 13, wherein the bioactive agent is an antimicrobial agent.

15. The dressing device according to claim 14, wherein the bioactive agent comprises one or more antimicrobial agents selected from the group consisting of chlorhexidine gluconate, chlorhexidine acetate, silver iodide, silver bromide, silver chloride, nano-particulate metallic silver, benzalkonium chloride, polyhexamethylene biguanide, Triclosan, metronidazole, alcohol, or iodine.

16. The dressing device of claim 15, wherein the bioactive agent is chlorhexidine gluconate.

17. The dressing device of claim 13, wherein the adhesive dressing has rounded corners.

18. The dressing device of claim 13, wherein the pad has a circular shape.

19. The dressing device of claim 13, wherein the adhesive dressing is at least partially transparent.

20. The dressing device of claim 13, wherein a quarter of the upper surface of the pad not encompassing the slit is attached to the wound facing side of the adhesive dressing at the area of the layer of adhesive disposed on the adhesive dressing exposed by the notch.

21. The dressing device of claim 13, wherein a size of the adhesive dressing is from about 3 cm squared to about 600 cm squared.

22. The dressing device of claim 13, wherein the liners each comprise a tab.

* * * * *